(12) United States Patent
Murphy

(10) Patent No.: US 9,028,543 B2
(45) Date of Patent: *May 12, 2015

(54) DEVICE VIEWABLE UNDER AN IMAGING BEAM

(71) Applicant: Kieran P. Murphy, Baltimore, MD (US)

(72) Inventor: Kieran P. Murphy, Baltimore, MD (US)

(73) Assignee: Kieran Murphy, LLC, Baltimore, MD (US)

( * ) Notice: Subject to any disclaimer, the term of this patent is extended or adjusted under 35 U.S.C. 154(b) by 12 days.

This patent is subject to a terminal disclaimer.

(21) Appl. No.: 13/919,537

(22) Filed: Jun. 17, 2013

(65) Prior Publication Data

US 2013/0282109 A1    Oct. 24, 2013

Related U.S. Application Data

(60) Continuation of application No. 13/047,226, filed on Mar. 14, 2011, now Pat. No. 8,465,539, which is a division of application No. 10/727,667, filed on Dec. 5, 2003, now Pat. No. 7,927,368, which is a continuation-in-part of application No. 10/394,007, filed on Mar. 24, 2003, now abandoned.

(60) Provisional application No. 60/366,529, filed on Mar. 25, 2002, provisional application No. 60/366,530, filed on Mar. 25, 2002.

(51) Int. Cl.

| *A61F 2/06* | (2013.01) |
| *A61B 17/12* | (2006.01) |
| *A61B 17/34* | (2006.01) |

(Continued)

(52) U.S. Cl.

CPC ............... *A61F 2/06* (2013.01); *A61B 10/0233* (2013.01); *A61B 17/12022* (2013.01); *A61B 17/12109* (2013.01); *A61B 17/12113* (2013.01); *A61B 17/12145* (2013.01); *A61B 17/3403* (2013.01); *A61B 17/3415* (2013.01); *A61B 19/081* (2013.01); *A61B 19/201* (2013.01); *A61B 19/54* (2013.01); *A61B 2017/1205* (2013.01); *A61B 2019/5236* (2013.01); *A61B 2019/5238* (2013.01); *A61B 2019/5454* (2013.01); *A61F 2/86* (2013.01); *A61L 31/18* (2013.01)

(58) Field of Classification Search

USPC ................. 623/1.42–1.46; 606/108, 194, 195

See application file for complete search history.

(56) References Cited

U.S. PATENT DOCUMENTS

| 3,721,997 A | 3/1973 | Mundt |
| 3,984,696 A | 10/1976 | Collica et al. |

(Continued)

FOREIGN PATENT DOCUMENTS

| CA | 2471958 | 6/2003 |
| DE | 3918736 | 12/1990 |

(Continued)

OTHER PUBLICATIONS

Dr. Hans-Ulrich Laasch et al., "Revision Notes for the FRCR Part 1", The Society of Radiologists in Training, 1999 (60 pages).

(Continued)

*Primary Examiner* — Vy Q Bui

(74) *Attorney, Agent, or Firm* — F. Chau & Associates, LLC

(57) ABSTRACT

The invention provides a stent made from a material operable to perform a stent's desired therapeutic functions, and also made from a material that has a radiopacity that substantially preserves the appearance of the stent when the stent is viewed under a CT imaging beam. Such a stent can allow for follow-up of the stent and the surrounding blood-vessel on CT.

9 Claims, 8 Drawing Sheets

(51) Int. Cl.
  *A61B 19/08*   (2006.01)
  *A61F 2/86*    (2013.01)
  *A61L 31/18*   (2006.01)
  *A61M 29/00*   (2006.01)
  *A61B 10/02*   (2006.01)
  *A61B 19/00*   (2006.01)

(56) References Cited

U.S. PATENT DOCUMENTS

| | | |
|---|---|---|
| 4,062,518 A | 12/1977 | Stivender et al. |
| 4,391,276 A | 7/1983 | Lazarus et al. |
| 4,465,069 A | 8/1984 | Barbier et al. |
| 4,533,356 A | 8/1985 | Bengmark et al. |
| 4,686,962 A | 8/1987 | Haber |
| 4,732,933 A | 3/1988 | Maeda et al. |
| 4,733,665 A | 3/1988 | Palmaz |
| 4,739,762 A | 4/1988 | Palmaz |
| 4,776,337 A | 10/1988 | Palmaz |
| 4,795,458 A | 1/1989 | Regan |
| 4,994,066 A | 2/1991 | Voss |
| 5,037,427 A | 8/1991 | Harada et al. |
| 5,064,435 A | 11/1991 | Porter |
| 5,067,957 A | 11/1991 | Jervis |
| 5,084,022 A | 1/1992 | Claude |
| 5,102,417 A | 4/1992 | Palmaz |
| 5,169,386 A | 12/1992 | Becker et al. |
| 5,211,165 A | 5/1993 | Dumoulin et al. |
| 5,242,455 A | 9/1993 | Skeens et al. |
| 5,292,339 A | 3/1994 | Stephens et al. |
| 5,311,883 A | 5/1994 | Sherman |
| 5,335,663 A | 8/1994 | Oakley et al. |
| 5,403,341 A | 4/1995 | Solar |
| 5,444,871 A | 8/1995 | Lopez |
| 5,482,043 A | 1/1996 | Zulauf |
| 5,499,418 A | 3/1996 | Tan et al. |
| 5,522,881 A | 6/1996 | Lentz |
| 5,522,882 A | 6/1996 | Gaterud et al. |
| 5,531,737 A | 7/1996 | Schade |
| 5,545,150 A | 8/1996 | Danks et al. |
| 5,546,961 A | 8/1996 | Harrison |
| 5,549,439 A | 8/1996 | Ploem |
| 5,549,635 A | 8/1996 | Solar |
| 5,556,414 A | 9/1996 | Turi |
| 5,562,726 A | 10/1996 | Chuter |
| 5,575,798 A | 11/1996 | Koutrouvelis |
| 5,590,655 A | 1/1997 | Hussman |
| 5,591,195 A | 1/1997 | Taheri et al. |
| 5,592,952 A | 1/1997 | Bohn |
| 5,607,467 A | 3/1997 | Froix |
| 5,609,629 A | 3/1997 | Fearnot et al. |
| 5,638,819 A | 6/1997 | Manwaring et al. |
| 5,676,159 A | 10/1997 | Navis |
| 5,693,015 A | 12/1997 | Walker et al. |
| 5,725,572 A | 3/1998 | Lam et al. |
| 5,735,892 A | 4/1998 | Myers et al. |
| 5,741,333 A | 4/1998 | Frid |
| 5,746,765 A | 5/1998 | Kleshinski et al. |
| 5,772,669 A | 6/1998 | Vrba |
| 5,788,626 A | 8/1998 | Thompson |
| 5,788,707 A | 8/1998 | Del Toro et al. |
| 5,797,952 A | 8/1998 | Klein |
| 5,800,517 A | 9/1998 | Anderson et al. |
| 5,810,870 A | 9/1998 | Myers et al. |
| 5,824,045 A | 10/1998 | Alt |
| 5,857,997 A | 1/1999 | Cimino et al. |
| 5,861,033 A | 1/1999 | Martakos et al. |
| 5,876,448 A | 3/1999 | Thompson et al. |
| 5,892,238 A | 4/1999 | Huttner et al. |
| 5,899,935 A | 5/1999 | Ding |
| 5,902,254 A | 5/1999 | Magram |
| 5,906,618 A | 5/1999 | Larson, III |
| 5,908,405 A | 6/1999 | Imran et al. |
| 5,922,020 A | 7/1999 | Klein et al. |
| 5,925,074 A | 7/1999 | Gingras et al. |
| 5,957,974 A | 9/1999 | Thompson et al. |
| 5,980,565 A | 11/1999 | Jayaraman |
| 5,989,280 A | 11/1999 | Euteneuer et al. |
| 6,010,529 A | 1/2000 | Herweck et al. |
| 6,059,759 A | 5/2000 | Mottola et al. |
| 6,086,610 A | 7/2000 | Duerig |
| 6,120,536 A | 9/2000 | Ding et al. |
| 6,126,654 A | 10/2000 | Giba et al. |
| 6,146,418 A | 11/2000 | Berman |
| 6,179,878 B1 | 1/2001 | Duerig et al. |
| 6,236,875 B1 | 5/2001 | Bucholz et al. |
| 6,270,523 B1 | 8/2001 | Herweck et al. |
| 6,283,125 B1 | 9/2001 | McNeirney et al. |
| 6,285,902 B1 | 9/2001 | Kienzle, III et al. |
| 6,298,110 B1 | 10/2001 | Ning |
| 6,315,791 B1 | 11/2001 | Gingras et al. |
| 6,325,538 B1 | 12/2001 | Heesch |
| 6,352,561 B1 | 3/2002 | Leopold et al. |
| 6,355,058 B1 | 3/2002 | Pacetti et al. ............. 623/1.15 |
| 6,374,937 B1 | 4/2002 | Galando et al. |
| 6,379,302 B1 | 4/2002 | Kessman et al. |
| 6,400,979 B1 | 6/2002 | Stoianovici et al. |
| 6,412,851 B1 | 7/2002 | Burks et al. |
| 6,423,089 B1 | 7/2002 | Gingras et al. |
| 6,428,557 B1 | 8/2002 | Hilaire |
| 6,447,540 B1 | 9/2002 | Fontaine et al. |
| 6,453,185 B1 | 9/2002 | O'Keefe |
| 6,456,684 B1 | 9/2002 | Mun et al. |
| 6,475,234 B1 | 11/2002 | Richter |
| 6,475,235 B1 | 11/2002 | Jayaraman |
| 6,481,888 B1 | 11/2002 | Morgan |
| 6,490,467 B1 | 12/2002 | Bucholz et al. |
| 6,490,475 B1 | 12/2002 | Seeley et al. |
| 6,511,471 B2 | 1/2003 | Rosenman et al. |
| 6,530,933 B1 | 3/2003 | Yeung et al. |
| 6,533,806 B1 | 3/2003 | Sullivan et al. |
| 6,544,041 B1 | 4/2003 | Damadian |
| 6,578,219 B1 | 6/2003 | Gabel et al. |
| 6,585,677 B2 | 7/2003 | Cowan, Jr. et al. |
| 6,629,992 B2 | 10/2003 | Bigus et al. |
| 6,635,064 B2 | 10/2003 | U et al. |
| 6,656,213 B2 | 12/2003 | Solem |
| 6,679,886 B2 | 1/2004 | Weikel et al. |
| 6,689,125 B1 | 2/2004 | Keith et al. |
| 6,716,238 B2 | 4/2004 | Elliott |
| 6,734,937 B2 | 5/2004 | Nakasogi et al. |
| 6,740,113 B2 | 5/2004 | Vrba |
| 6,857,778 B2 | 2/2005 | Mun et al. |
| 6,932,787 B2 | 8/2005 | Cowan et al. |
| 6,961,606 B2 | 11/2005 | DeSilets et al. |
| 7,391,042 B2 | 6/2008 | Goldstein |
| 2001/0041928 A1 | 11/2001 | Pavcnik et al. |
| 2002/0002383 A1 | 1/2002 | Sepetka et al. |
| 2002/0022825 A1 | 2/2002 | Saitou et al. |
| 2002/0040239 A1 | 4/2002 | Murayama et al. |
| 2002/0052640 A1 | 5/2002 | Bigus et al. |
| 2002/0077540 A1 | 6/2002 | Kienzle |
| 2002/0183610 A1 | 12/2002 | Foley et al. |
| 2002/0183763 A1 | 12/2002 | Callol et al. |
| 2002/0196906 A1 | 12/2002 | Mun et al. |
| 2003/0004563 A1 | 1/2003 | Jackson et al. |
| 2004/0073286 A1 | 4/2004 | Armstrong et al. |
| 2004/0082905 A1 | 4/2004 | Solar et al. |
| 2004/0148000 A1 | 7/2004 | Bilge |
| 2004/0176682 A1 | 9/2004 | Murphy |
| 2004/0176833 A1 | 9/2004 | Pavcnik et al. |
| 2004/0176835 A1 | 9/2004 | Vrba |
| 2004/0241094 A1 | 12/2004 | Chung et al. |
| 2006/0104999 A1 | 5/2006 | Chung et al. |
| 2006/0134144 A1 | 6/2006 | Chung et al. |
| 2008/0182282 A1 | 7/2008 | Markman et al. |

FOREIGN PATENT DOCUMENTS

| | | |
|---|---|---|
| EP | 0 797 988 A2 | 10/1997 |
| EP | 0578988 | 10/1997 |
| EP | 0578988 A1 | 10/1997 |
| EP | 0578998 | 10/1997 |
| EP | 0797988 | 10/1997 |

(56) References Cited

FOREIGN PATENT DOCUMENTS

| | | |
|---|---|---|
| EP | 0809998 | 12/1997 |
| EP | 0809998 A2 | 12/1997 |
| EP | 0 872 220 A1 | 10/1998 |
| EP | 0872220 | 10/1998 |
| EP | 947204 | 10/1999 |
| EP | 947204 A2 | 10/1999 |
| EP | 0947204 | 12/2000 |
| EP | 1 155 689 A2 | 11/2001 |
| EP | 1155689 | 11/2001 |
| EP | 1362603 | 11/2003 |
| EP | 1362603 A | 11/2003 |
| WO | 9826731 | 6/1998 |
| WO | WO 98/26731 | 6/1998 |
| WO | 0024338 | 5/2000 |
| WO | WO 00/24338 | 5/2000 |
| WO | WO 0040159 | 7/2000 |
| WO | 03094798 | 11/2003 |
| WO | 03094798 A | 11/2003 |

OTHER PUBLICATIONS

A.C. Kak and Malcolm Slaney, "Principles of Computerized Tomographic Imaging", Chapter 4 (Measurement of Projection Data-The Nondiffracting Case), pp. 113-134, IEEE, 1988 (22 pages).

Anthony R. Kovscek et al., "Stanford University Petroleum Research Institute Preliminary Twenty-Fourth Annual Report", Apr. 19-21, 2001 (68 pages).

Google's Cache of http://www.bicetre.neuroradio.net/french/journal/menu.htm. at http://www.google.com/search?q=cacheU20CIRBv7hYC; www.bicetre.neuroradio.net/french/journal/menu.htm+MCTA+angiography&hl=en&ie+UTF8, Index MARS 2002 (5 pages).

Gailloud, P.; Hillis, A.; Perler, B.; and Murphy, K.J. "Vertebrobasilar Stroke as a Late Complication of a Blalock-Taussig Shunt", Wiley-Liss, Inc., 2002, pp. 231-234 (4 pages).

Google's Cache of http://wwvv.google.ca/search?q=%houndsfield+unit% 22&ie=Utf-8&oe=UTF8&hl=en&meta=, Mar. 21, 2003 (60 pages).

Dolmatch, Bart, M.D., et al., "Patency and Tissue Response Related to Two Types of Polytetrafluoroethylene-Covered Stents in the Dog," Journal of Vascular and Interventional Radiology, vol. 7, No. 5, Sep.-Oct. 1996, pp. 642-649 (9 pages).

Michael Strotzer, MD, et al., "Appearance of Vascular Stents in Computed Tomographic Angiography: In Vitro Examination of 14 Different Stent Types," Investigative Radiology, vol. 36: (11) p. 652-658, Nov. 2001, (6 pages).

Stefan Hahnel, et al., "Small-Vessel Slants for Intracranial Angioplasty: In Vitro Comparison of Different Stent Designs and Sizes by Using CT Angiography," AJNR Am J Neuroradiol 24:1512-1516, Sep. 2003 (6 pages).

David Maintz, et al., "Revealing In-Stent Stenoses of the Iliac Arteries: Comparison of Multidetector CT with MR Angiography and Digital Radiographic Angiography in a Phantom Model," AJR:179, p. 1319-1322, Nov. 2002 (4 pages).

Henry Brenn, et al., "Polymer-Based Drug Delivery to the Brain," Science & Medicine, Inc., vol. 3, No. 4, p. 1-11, Jul./Aug. 1996 (11 pages).

Stephen Schroeder, et al., "Influence of Heart Rate on Vessel Visibility in Noninvasive Coronary Angiography Using New Multislice Computed Tomography Experience in 94 Patients," Journal of Clinical Imaging 26 (2002), p. 106-107, 2002 (2 pages).

Paul P. Wang, et al., "Local Drug Delivery to the Brain," Advanced Drug Delivery Review 54 (2002), p. 987-1013, 2002 (27 pages).

Antezanna DF, et al., "High-dose Ibuprofen for reduction of striatel infarets during middle cerebral artery occlusion in rats," http://www.ncbi.nlm.nih.gov:80/entrez/query.fcgi?cmd=PubMed&list_uids+12691413&dopt=Abstract; last visited on Oct. 1, 2003 (2 pages).

Patrik Gabikian, MD, et al., "Stroke: Prevention of Experimental Cerebral Vasospasm by Intracranial Delivery of a Nitric Oxide Donor From a Controlled-Release Polymer," http://stroke.ahajournals.org/cgi/content/full/33/11/2681, last visited on Oct. 1, 2003 (11 pages).

Travis S. Tiemey, et al., "Prevention and Reversal of Experimental Posthemorrhagic Vasospasm by the Periadventitial Administration of Nitric Oxide From a Controlled-release Polymer," http://www.neurosurgery-online/fulltext/4904/0945/NURO49040945_doc.html, vol. 49, No. 4, Oct. 2001 (11 pages).

Rafael J. Tamargo, et al., "The Intracerebral Administration of Phenytoin Using Controlled-Release Polymers Reduces Experimental Seizures in Rats," Epilepsy Research 48, p. 145-155; 2002 (11 pages).

J. Golzarian, "Imaging After Endovascular Repair of Abdominal Aortic Aneurysm," Abdominal Imaging 28, p. 236-243, 2003 (8 pages).

Jens Rodenwaldt, "Multislice Computed Tomography of the Coronary Arteries," Eur Radial (2003) 13:748-757, Jan. 2003 (10 pages).

Stefanie Weigel, et al., "Thoracic Aortic Stent Graft: Comparison of Contrast-Enhanced MR Angiography and CT Angiography in the Follow-Up: Initial Results," Eur Radiol (2003) 13:1628-1634, Feb. 2003, (7 pages).

Quoc-Anh Thai, BA, et al., "Inhibition of Experimental Vasospasm in Rats with the Periadventital Administration of Ibuprofen Using Controlled-Release Polymers," published by American Heart Association, p. 140-147, Jan. 1999 (8 pages).

Langer R. Brem, et al., "Biocompatibility of Polymeric delivery systems for macromolecules," http://www.ncbi.nlm.nih.gov:80/entrez/query.fcgi?cmd=Retrieve&db=PubMed&list_uids=7348718&dopt=Abstract, last visited on Oct. 31, 2003 (1 page).

H. Brem, et al., "Biocompatibility of a biodegradable, controlled-release polymer in the rabbit brain," http://www.ncbi.nlm.nih.gov:80/entrez/query.fcgi?cmd=Retrieve&db=PubMed&list_uids=2772427&dopt=Abstract, last visited on Oct. 3, 2003 (1 page).

Seung-Jung Park, M.D., et al., "A Paclitaxel-Eluting Stent for the Prevention of Coronary Restenosis," The New England Journal of Medicine, vol. 348:1537-1545, No. 16, Apr. 17, 2003, (3 pages).

Allan W. Heldman, MD, et al., "Paclitaxel Stent Coating Inhibits Neointimal Hyperplasia at 4 weeks in a Porcine Model of Coronary Restenosis," published by American Heart Association, Inc., p. 2289-2295, May 2001 (7 pages).

Jonette Foy, Ph.D., "Drug-Eluting Stents: Pre-Clinical Standards & Recommended Studies," FDA/SIR Device Forum Meeting, Nov. 2002 (7 pages).

Munshi I, Lathrop D, Madsen JR, Frim DM; "Intraventricular Pressure Dynamics in Patients with Ventriculopleural Shunts: A Telemetric Study"; Pediatric Neurosurgery; 1998; vol. 28; pp. 67-69.

Jose M. Montes, MD; John H. Wong, MD; Pierre B. Fayad, MD Issam A. Awad, MD; "Stereotactic Computed Tomographic—Guided Aspiration and Thrombolysis of Intracerebral Hematoma" Stroke. Apr. 2000; vol. 31: pp. 834-840.

Neal J. Naff, MD; Juan R. Carhuapoma, MD; Michael A. Williams, MD; Anish Bhardwaj, MD; John A. Ulatowski, MD, PhD; Joshua Bederson, MD; Ross Bullock, MD; Erich Schmutzhard, MD; Bettina Pfausler, MD; Penelope M. Keyl, PhD; Stanley Tuhrim, MD Daniel F. Hanley, MD ; "Treatment of Intraventricular Hemorrhage With Urokinase Effects on 30-Day Survival"; Stroke. Apr. 2000; vol. 31: pp. 841-847.

Miyake, Hiroji MD; Ohta, Tomio MD; Kajimoto, Yoshinaga MD; Matsukawa, Masanori MD; "A New Ventriculoperitoneal Shunt with a Telemetric Intracranial Pressure Sensor: Clinical Experience in 94 Patients with Hydrocephalus"; Neurosurgery. 40(5):931-935, May 1997.

Munshi I, Lathrop D, Madsen Jr, Frim DM; "Intraventricular Pressure Dynamics in Patients with Ventriculopleural Shunts: A Telemetric Study"; Pediatric Neurosurgery; 1998; vol. 28; pp. 67-69.

Miyake, Hiroji MD; Ohta, Tornio MD; Kajimoto, Yoshinaga MD; Matsukawa, Masanori MD; "A New Ventriculoperitoneal Shunt with a Telemetric Intracranial Pressure Sensor: Clinical Experience in 94 Patients with Hydrocephalus"; Neurosurgery. 40(5):931-935, May 1997.

Office Action dated Jul. 1, 2010 for U.S. Appl. No. 11/081,494.

European Patent Application No. EP 04 81 2874 Search Report dated Decemebr 18, 2008.

(56) References Cited

OTHER PUBLICATIONS

FOSSA medical: Welcome to Fossa medical.com at URL <http://www.fossamedical.com/news.htm> from Sep. 9, 2005 [retrieved on Sep. 18, 2008].
Stone Sweeper ® Kidney Stone Removal Device: The Clear Path to Ureteral Patency—insertion instructions, at URL <http://www.fossamedical.com/pdfs/sweepersurgicaltechnique.Pdf>, 2004, [retrieved on Sep. 18, 2008].
Drake et al., The Shunt Book, COPYRGT. 1995 Blackwell Science Inc. Massachusetts.
Kopp A F, Ohnesorge B, Flohr T, Georg C, Schroeder S, Kuttner A, Martensen,J, Claussen C D., Cardiac multidetector-row CT: first clinical results of retrospectively ECG-gated spiral with optimized temporal and spatial resolution, Rofo Fortschr Geb Rontgenstr Neuen Bildgeb Verfahr. May 2000; 172(5):429-35.
Ohnessorge B, Flohr T, Becker C, Knex A, Kopp A F, Fukuda K. Reiser M F., Cardiac imaging with rapid, retrospective ECG synchronized multilevel spiral CT Radiologe, Feb. 2000:40(2): 111-7.
Achenbach S, Moshage W, Ropers D, Nossen J, Bachmann K, Noninvasive coronary angiography with electron beam tomography: methods and clinical evaluation in post-PTCA follow-up Z Kardiol., Feb. 1997; 86(2):121-30.
Becker C R, Schoepf U J, Reiser M F., Methods for quantification of coronary artery calcificatins with electron beam and conventional CT and pushing the spiral CT envelope: new cardiac applications. Int J Cardiovasc Imaging, Jun. 17, 2001;(3):203-11.
Kopp A F, Schroeder S, Kuettner A, Baumbach A, Georg C, Kuzo R, Heuschmid M, Ohnesorge B, Karsch K R, Claussen C D, Noninvasive coronary angiography with high resolution multidetector-row computed tomography. Results in 102 patients. Eur Heart J. Nov. 23, 2002;(21): 1714-25.
Achenbach S, Ulzheimer S,Baum U, Kachelriess M. Ropers D, Giesler T. Bautz W, Daniel W G, Kalender W A, Moshage W, Noninvasive coronary angiography by retrospectively ECG-gated multislice spiral CT. Circulation. Dec. 5, 2000:102(23):2823-8.
Knez A, Becker A, Becker C, Leber A, Boekstegers P, Reiser M, Steinbeck G Detection of coronary calcinosis with multislice spiral computerized tomography: an alternative to electron beam tomography Z Kardiol. Aug. 2002:91 (8):642-9.
Mahnken A H, Sinha A M, Wildberger J E, Krombach G A, Schmitz-Rode T, Gunther R W, The influence of motion artifacts conditioned by reconstruction, on the coronary calcium score in multislice spiral CT, Rofo Fortschr Geb Rontgenstr Neuen Bildgeb Verfahr, Oct. 2001;173(10):888-92 1111.
Moses et al., Sirilumus eluting stents versus stanrd stents in patients with stenosis of the coronary artery, New England Journal of Medicine, p. 1315-1323 Oct. 2, 2003 vol. 349, No.
Office Action dated Feb. 28, 2012 for U.S. Appl. No. 11/081,494.
Choquette et al. Direct Selenium X-Ray Detector for Fluoroscopy, R&F, and Radiography, 2000, In Medical Imaging 2000: Physics of Medical Imaging, Proceedings of SPIE vol. 3977, pp. 128-136.
Canadian Office Action dated Mar. 9, 2011 for Application No. 2,455,439.
Lee, Y., et al, Synthesis of 188 Re-labelled long chain alkyl diaminedithiol for therapy of liver cancer, Nuclear Medicine Communications, Mar. 2002—vol. 23, Issue 3, pp. 237-242.
Jose M. Montes, MD; John H. Wong, MD; Pierre B. Fayad, MD; Issam A. Awad, MD; Stereotactic Computed Tomographic-Guided Aspiration and Thrombolysis of Intracerebral Hematoma Stroke Apr. 2000; vol. 31: pp. 834-840.
Neal J. Naff, MD; Juan R. Carhuapoma, MD; Michael A. Williams, MD; Anish Bhardwaj, MD; John A. Ulaowski, MD, PhD; Joshua Bederson, MD; Ross Bullok, MD; Eric Schmutzhard, MD; Bettina Pfausler, MD; Penelope M. Keyl, PhD; Stanley Tuhrim, MD; Daniel F. Hanley, MD; "Treatment of Intraventricular Hemorrhage With Urokinase Effects on 30-Day Survival"; Stroke. Apr. 2000; vol. 31 pp. 841-847.
Miyake, Hiroji MD; Ohta, Tomio MD; Kajimoto, Yoshinaga MD; Matsukawa, Masanori MD; "A New Ventriculoperitoneal Shunt with a Telemetric Intracranial Pressure Sensor: Clinical Experience in 94 Patients with Hydrocephalus"; Neurosurgery. 40(5): 931-935, May 1997.
A.C. Kak Malcolm Slaney, "Principles of Computerized Tomographic Imaging", Chapter 4 (Measurement of Projection Data—The Nondiffracting Case), pp. 113-134, IEEE, 1988.
Google's Cache of http://www.bicetre.neuroradio.net/french/journal/menu.htm. at http://www.google.com/search?q=cacheU20QRBv7hYC; www.bicetre.neuroradio.net/french/journal/menu.htm=MCTA+angiography&hi=en&ie+UTF8, Index MARS 2002 (5 pages).
Gailloud P. Hillis, A., Perler, B.; and Murphy, K.J. "Vertebrobasilar Stroke as a Late Complication of a Blalock-Taussig Shunt", Wiley-Liss, Inc., 2002, pp. 231-234.
Google's Cache of http://www.google.ca/search?q=%houndsfield+unit%22&ie=UTF-8&oe=UTF8&hl=en&meta=, Mar. 21, 2003 (60 pages).
Dolmach, Bart, MD., et al., "Patency and Tissue Response Related to Two Types of Polytetrafluroethylene-Covered Stens in the dog, "Journal of Vascular and Interventional Radiology, vol. 7 No. 5 Sep.-Oct. 1996, pp. 642-649.
Michael Strotzer, MD., et al. "Appearance of Vascular Stents in Computed Tomographic Angiography: In Vitro Examination of 14 Different Stent Types," Investigative Radiology, vol. 36: (11) pp. 652-658, Nov. 2001.
Stefan Hahnel, et al., "Small-Vessel Stents for Intracranial Angioplasty: In Vitro Comparison of Different Stent Designs and Sizes by Using CT Angiography, "AJNR AM J Neuroradiol 24:1512-1516, Sep. 2003.
David Maintz et al., "Revealing in_Stent Stenoses of the Iliac Arteries: Comparison of Multidetector CT with MR Angiography and Digital Radiographic Angiography in A Phantom Model," AJR:179, p. 1319-1322, Nov. 2002.
Henry Brem, et al. "Polymer-Based Drug Delivery to the Brain, "Science & Medicine, Inc., vol. 3, No. 4, p. 1-11, Jul./Aug. 1996.
Stephen Schroeder, et al. "Influence of Heart Rate on Vessel Visibility in Noninvasive Coronary Angiography Using New Multislice Computed Tomography Experience in 94 Patients," Journal of Clinical Imaging 26 (2002), pp. 106-107.
Paul P. Wang et al., "Local Drug Delivery to the Brain," Advanced Drug Delivery Review 54 (2002) pp. 987-1013.
Antezanna DF, et al., "High-dose Ibuprofen for reduction of striatal infarets during middle cerebral artery occlusion in rats,"http://www.ncbi.nlm.nih.gov:80/entrez/query.fcgi?cmd=PubMed&list-uids+12691413&dopt=Abstract; last visited on Oct. 1, 2003 (2 pages).
Patrik Gabikian, MD et al., "Stroke: Prevention of Experimental Cerebral Vasospasm by Intracranial Delivery of Nitric Oxide Donor From Controlled-Release Polymer, "http://stroke.ahajournals.org/cgi/content/full/33/1/12681, last visited on Oct. 1, 2003 (11 pages).
Travis S. Tierney, et al., "Prevention and Reversal of Experimental Posthemorrhagic Vasospasm by the Periadventitial Administration of Nitric Oxide From a Controlled-release Polymer," http://www.neurosurgery-online/fulltext/4904/0945/NUR049040945-doc.html, vol. 49 No. 4, Oct. 2001 (11 pages).
Rafael J. Tamargo, et al. "The Intracerebral Administration of Phenytoin Using Controlled-Release Polymers Reduces Experimental Seizures in Rats," Epilepsy Research 48, p. 145-155 (2002).
J. Golzarian, Imaging After Endovascular Repair of Abdominal Aortic Aneurysm, Abdominal Imaging 28, p. 236-243 (2003).
Jens Rodenwaldt, Multislice Computed Tomography of the Coronary Arteries, Eur Radiol (2003) 13:748-757, Jan. (2003).
Stefanie Weigel et al., "Thoracic Aortic Stent Graft: Comparison of Contrast-Enhanced MR Angiography and CT Angiography in the Follow-Up: Initial Results, "Eur Radiol (2003) 13: 1628-1634, Feb. 2003.
Quoc-Anh Thai, BA et al., "Inhibition of Experimental Vasospasm in Rats with the Periadventital Administration of Ibprofen Using Controlled-Release Polymers," published by American Heart Association, pp. 140-147 Jan. 1999.
Langer R. Brem et al., "Biocompatibility of Polymeric Delivery System for Macromolecules, "http://www.ncbi,nlm.nlh.gov:80/

(56) References Cited

OTHER PUBLICATIONS entrez/query.fcgi?cmd=Retrieve&db=PubMedlist-uids+2772427&dopt=Abstract, last visited on Oct. 3, 2003 (1 page).

Seung-Jung Park, MD., et al., "A Paclitaxel-Eluting Stent for the Prevention of Coronary Restenosis," The New England Journal of Medicine, vol., 348:1537-1545 No. 16, Apr. 17, 2003.

Allan W. Heldman, MD et al., Paclitaxel Stent Coating Inhibits Neointimal Hyperplasia at 4 weeks in Porcine Model of Coronary Restenosis, published by the American Heart Association, Inc., pp. 2289-2295, May 2001.

Jonette Foy, Phd., "Drug-Eluting Stents: Pre-Clinical Standards & Recommended Studied." FDA/SIR Device Forum Meeting, Nov. 2002.

Drake et al. The Shunt Book, Copyright 1995 Blackwell Science in Massachusettes.

Kopp A F, Ohnsesorge B, Flohr T, Georg C. Schroeder S. Kuttner A, Martensen, J. Claussen CD Cardiac multidetector-row CT; First Clinical Results of retrospectively ECG-gated spiral with optimized temporal and spatial resolution, Rofo Fortschr Geb Rotgenstr Neuen Bildgeb Verfahr May 2000 172(5) 429-35.

Ohnessorge B, Flohr T. Becker C, Knex A, Knopp A F Fukada K Reiser M F Cardiac Imaging with rapid, retrospective ECG Synchronized multilevel spiral CT Radiologe, Feb. 200; 40 (2) 111-7.

Achenbach S. Moshage W, Ropers D, Nossen J Bachmann K, Noninvasive Coronary Angiography with Electron Beam Tomography: Methods and Clinical Evaluation in Post-PTCA Follow-up Z Kardiol, Feb. 1997; 86(2) 121-30.

Becker C R, Schoepf U J, Reiser M F., Methods for Quantification of Coronary Artery Calsifications with Electrogram Beam and Conventional CT and Pushing the Spiral CT Envelope; New Cardiac Applications, Int J. Cardiovasc Imaging Imaging, Jun. 17, 2001; (3): 203-11.

Kopp A F, Schroeder S, Kuettner A, Baumbach A Georg C, Kuzo R, Heuschmid M, Ohnesorge B, Karsch K R, Claussen C D, Noninvasive Coronary Angiography with High Resolution Multidetector-Row Computed Tomography Results in 102 Patients, Eur Heart J., Nov. 23, 2002; (21); 1714-25.

Achenbach S, Ulzheimer S, Baum U, Kachelriess M, Ropers D, Giesler T, Bautz W. Daniel W G, Kalender W A, Moshage W, Noninvasive Coronary Angiography by Retrospectively ECG-Gated Multislice Spiral CT, Circulation, Dec. 5,2000: 102(23):2823-8.

Knez A, Becker A, Becker C, Leber A Boekstegers P, Reiser M, Steinbeck G., Detection of Coronary Calcinosis with Multislice Spiral Computerization Tomography: An Alternative to Electron Bean Tomography, Z. Kardiol, Aug. 2002:01 (8): 642-9.

Mahnken A H, Sinha A M, Wildberger J E, Krombach G A , Schmitz-Rode T, Gunther R W , The Influence of Motion Artifacts Conditioned by Reconstruction, on the Coronary Clacium Score in Multislice Spiral CT, Rofo Fortschr Geb Rontgenstr Neuen Bildgeb Verahr, Oct. 2001; 173(10): 888-92.

Moses et al., Sirlumus Eluting Stents Versus Standard Stents in Patients with Stenosis of the Coronary Artery, New England Journal of Medicine, p. 1315-1323, Oct. 2, 2003 vol. 349.

Fossa Medical Welcome to Fossa Medical.com @ URL <http://www.fossamedical.com/news.htm. from Sep. 9, 2005 (retrieved on Sep. 18, 2008).

Stone Sweeper (r) Kidney Stone Removal Device: The Clear Path to Ureteral Patency—Insertion Instructions, at URL<http://www.fossamedical.com/pdfs/sweepersurgicaltechnique.pdf>, 2004 (retrived on Sep. 18, 2008).

H. Brem, et al. Biocompatibility of Biodegradable controlled released polymer in the rabbit brain, http://www.ncbi.nlm.nih.gov:80/entrz/guery.fcgi?cmd=Retrieve&db=PubMed&list_uids=2772427&dopt=Abstract, last visited on Oct. 3, 2003 (1page).

Lee, Y. et al., Synthesis of 188Re-labelled long chain alkyl diaminedithiol for therapy of liver cancer, Nuclear Medicine Communications, Mar. 2002—vol. 23, Issue 3, pp. 237-242.

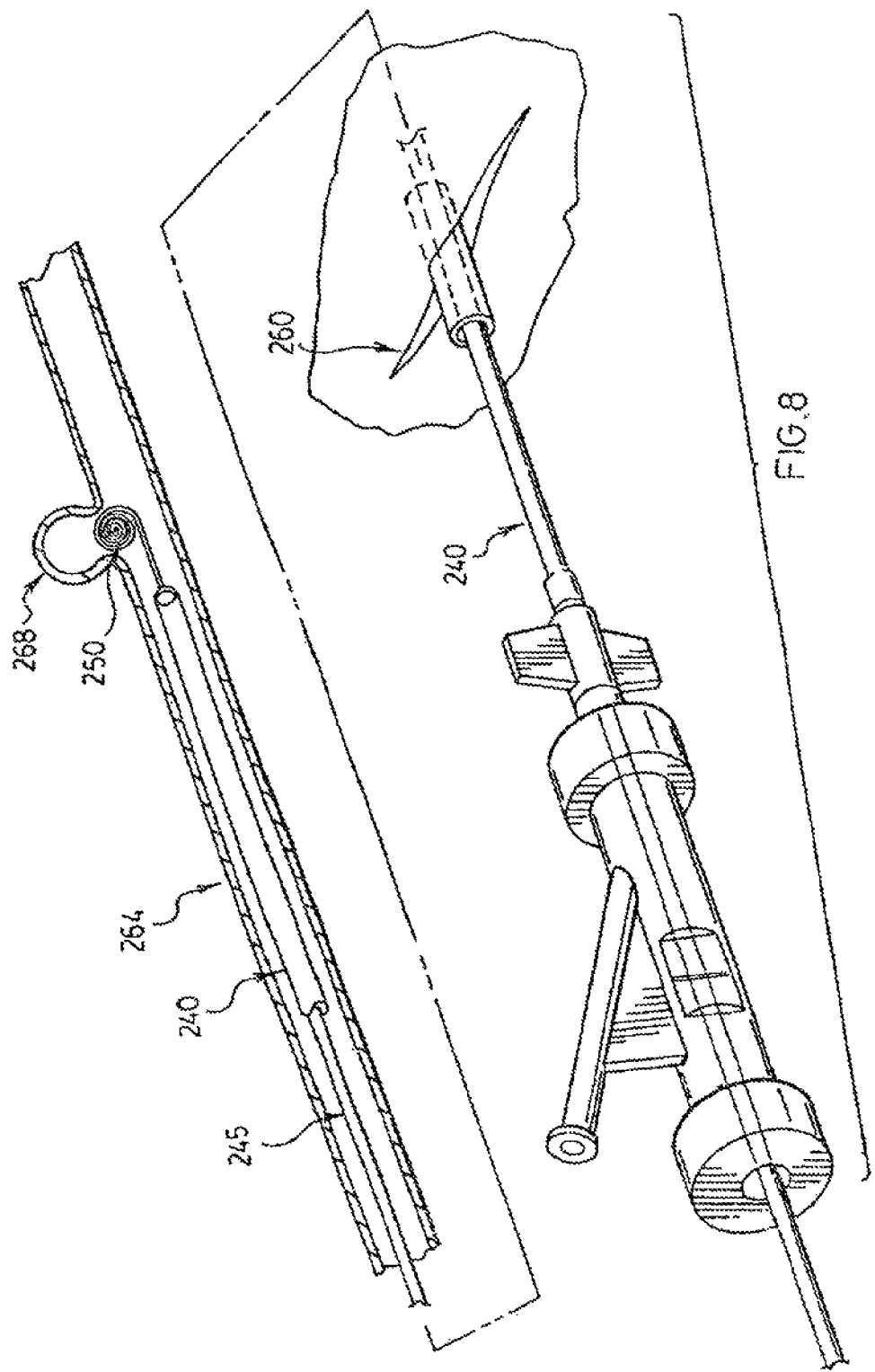

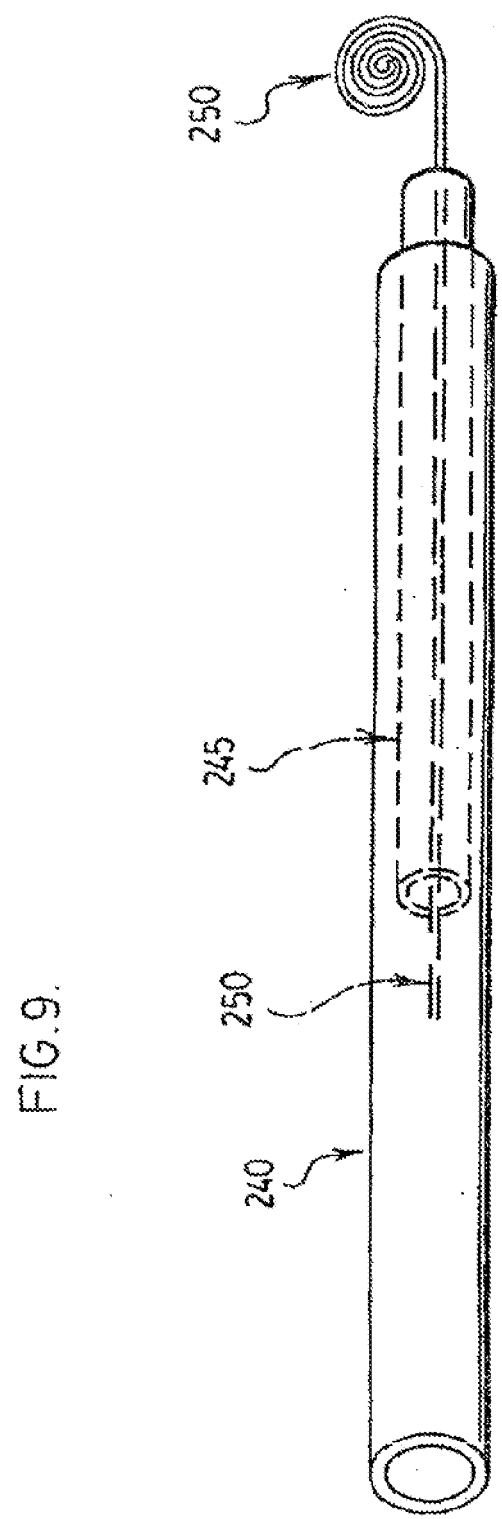

DEVICE VIEWABLE UNDER AN IMAGING BEAM

CROSS-REFERENCE TO RELATED APPLICATIONS

This application is a Continuation Application of U.S. patent application Ser. No. 13/047,226 filed Mar. 14, 2011, which is a Divisional Application of U.S. patent application Ser. No. 10/727,667 filed on Dec. 5, 2003, now U.S. Pat. No. 7,927,368, which is a Continuation-In-Part of U.S. patent application Ser. No. 10/394,007 filed Mar. 23, 2003, now abandoned, and claims priority to U.S. Patent Application Ser. No. 60/366,530 filed Mar. 25, 2002 and U.S. Patent Application Ser. No. 60/366,529 filed Mar. 25, 2002, the disclosures of each of which are hereby incorporated herein by reference in their entireties.

FIELD OF THE INVENTION

The present invention relates generally to surgery under image guided navigation and more particularly relates to a method, device and system for surgical implantation of a medical device or the like, and/or postoperative evaluation of an implanted medical device or the like under image guidance.

BACKGROUND OF THE INVENTION

Stroke and cardiac disease remain a major cause of morbidity and result in profound suffering and expense. Increased awareness and improvements in diagnostic procedures have significantly increased the diagnosis of cervical and intracranial and cardiac vascular stenosis. A vascular stenosis is now being treated endovascularly at a significantly increased frequency. However, follow-up has predominantly been by angiography which evaluates the vascular contour but not the vascular wall. It is invasive, time consuming and expensive. Preliminary studies suggest that stent evaluation and restenosis pathophysiology can also be evaluated with Multi-detector Computed Tomography Angiography ("MDCTA") which would be a significant advantage of this technique over conventional angiography.

More specifically, endovascular therapy has ushered in a new age of minimally invasive vascular treatment. Endovascular devices have been rapidly developed and refined. Present technologies have enabled precise deployment of stents in much smaller arteries and have become more flexible and compliant so they can be navigated through tortuosities. At the same time there has been a growing pool of physicians trained in modern endovascular therapies so services are more widely available. However, the monitoring of these patients has become suboptimal because it relies on conventional angiography which is invasive and expensive. It also requires the patient to spend a full day removed from their daily activities. It also requires that some patients on anticoagulation briefly discontinue their therapy or be admitted to the hospital for an extended period of time. New MDCTA technology has not been widely used or validated for follow up. However, preliminary case studies seem to indicate that this technology is likely to provide additional beneficial information about the vascular wall and stent not obtainable from conventional angiograms. MDCTA is also non-invasive, requires a minimal amount of time and is less costly. MDCTA now has an axial resolution less than 0.5 mm and with the proposed development of new protocols and algorithms for image processing, this will be a superior tool to evaluate stenting and the etiology of any restenosis or stent failures. In particular, it will likely be able to separate negative remodeling from neointimal growth. It will also be able to evaluate for stent deformity and wall apposition as well as remodeling. MDCTA should also be applicable to other endovascular procedures such as follow up for aneurysm coilings.

Indeed MDCTA reflects a number of advances in medical imaging that allow real time and/or three-dimensional image gathering under Computed Tomography ("CT"), Magnetic Resonance Imaging ("MRI") or the like. For example, CT scanners such as the Toshiba Acquillion multi detector are capable of generating images in three different areas at frame rates of 13 frames a second, to thereby generate a three-dimensional rendering of the target area. Indeed, this and other advances in CT have led to the development of new CT applications including CT Angiography ("CTA"), and CT Perfusion ("CTP"). These imaging modalities are rapidly developing into powerful tools in the diagnosis and treatment of both ischemic and hemorrhagic stroke and bilary occlusion. See, for example, the following prior art references: [0006] Kopp A F, Ohnesorge B, Flohr T, Georg C, Schroder S, Kuttner A, Martensen J, Claussen C D. [Cardiac multidetector-row CT: first clinical results of retrospectively ECG-gated spiral with optimized temporal and spatial resolution] Rofo Fortschr Geb Rontgenstr Neuen Bildgeb Verfahr. 2000 May; 172(5):429-35. [0007] Ohnesorge B, Flohr T, Becker C, Knez A, Kopp A F, Fukuda K, Reiser M F. [Cardiac imaging with rapid, retrospective ECG synchronized multilevel spiral CT] Radiologe. 2000 February; 40(2):111-7 [0008] Achenbach S, Moshage W, Ropers D, Nossen J, Bachmann K. Non-invasive coronary angiography with electron beam tomography: methods and clinical evaluation in post-PTCA follow-up Z Kardiol. 1997 February; 86(2):121-30. [0009] Becker C R, Schoepf U J, Reiser M F. Methods for quantification of coronary artery calcifications with electron beam and conventional CT and pushing the spiral CT envelope: new cardiac applications. Int J Cardiovasc Imaging, 2001 June; 17(3):203-11. [0010] Kopp A F, Schroeder S, Kuettner A, Baumbach A, Georg C, Kuzo R, Heuschmid M, Ohnesorge B, Karsch K R, Claussen C D. Non-invasive coronary angiography with high resolution multidetector-row computed tomography. Results in 102 patients. Eur Heart J. 2002 November; 23(21):1714-25. [0011] Achenbach S, Ulzheimer S, Baum U, Kachelriess M, Ropers D, Giesler T, Bautz W, Daniel W G, Kalender W A, Moshage W. Non-invasive coronary angiography by retrospectively ECG-gated multislice spiral CT. Circulation. 2000 Dec. 5; 102(23):2823-8. [0012] Knez A, Becker A, Becker C, Leber A, Boekstegers P, Reiser M, Steinbeck G. [Detection of coronary calcinosis with multislice spiral computerized tomography: an alternative to electron beam tomographyZ Kardiol. 2002 August; 91(8):642-9. [0013] Mahnken A H, Sinha A M, Wildberger J E, Krombach G A, Schmitz-Rode T, Gunther R W. [The influence of motion artifacts conditioned by reconstruction, on the coronary calcium score in multislice spiral CT] Rofo Fortschr Geb Rontgenstr Neuen Bildgeb Verfahr. 2001 October; 173 (10):888-92.

However, despite these advances in medical device technology, and in particular stent technology and imaging technology, prior art stent technologies have certain limitations when viewed under such CT machines, particularly due to beam hardening artefacts that are typically present, which thereby obscure the image and obviate or reduce the effectiveness of the CT machine as a post-operative diagnostic tool Due to these present limitations using MDCTA, it is common to rely on classical angiography for postoperative evaluation of endovascular procedures, yet such angiographic methods are invasive and expensive. In the USA, an angiogram can cost up to $8000.00, yet a corresponding MDCTA could be offered for as little as $400.00. Additionally, endovascular ultrasound has significant associated risks and is not suitable for the small intracranial vessels. In the end, it is believed that MDCTA has the potential to provide good visualization of the lumen as well as the arterial wall and stent. MDCTA actually visualizes the stent better than fluoroscopy and will likely prove to be the preferred technique when background subtraction is used to increase vascular conspicuity. It is also believed that MDCTA would also enable more precise outcome evaluation and allow for investigation of the underlying pathophysiology as well as evaluation of the stents and devices used.

Polymer or lipid based drug delivery systems that can deliver drugs at a defined rate for up to five years from a single treatment have revolutionized medical therapy. Drug coated coronary stents have been shown to decrease restenosis rates in large clinical trials. See for example, the following references: [0017] "Sirilimus eluting stents versus standard stents in patients with stenosis of the coronary artery", Moses et al. New England Journal of Medicine, page 1315-1323 Oct. 2, 2003 Vol. 349, No. 14. [0018] "Paclitaxel stent coating inhibits meointimal hyperplasia at 4 weeks in a porcine model of restenosis", Heldman et al. circulation 2001, 103-2289-95. [0019] "A Paclitaxel eluting stent for the prevention of coronary restenosis", Park et al. New England Journal of Medicine 2003, Vol. 348, page 1537-45.

With respect to the drug delivery systems there are several types available at this time. These are principally those that are biodegradeable or those that are non biodegradeable. Biodegradable polymers release their loaded agents as they break down, while the matrix of non-biodegradable polymers remain intact even after all of the therapeutic agent has been released. These polymers release their loaded material by a process of either bulk erosion or surface erosion and diffusion or degradation. The polymers and co-polymers that are available at the present time include ethylene vinyl acetate ("EVAc"), a hydrophilic non biodegradable polymer, and biodegradeable polymers such as hydrophobic polymers such as poly[BIS(p-carboxyphenoxy)]propane-sebacic acid ("PCPP:SA"), hydrophilic polymers and fatty acid dimer-sebacic acid ("FAD:SA") polymers that deliver drugs including hydrophilic drugs and compounds A process such as lyophilization can be used to load the polymer with the desired compound or drug or compounds or drugs. In this was PCPP:SA, a desired compound such as iodinated contrast material, and methyl chloride may undergo the lyophilization process to load the PCPP:SA with a material with the ability to attenuate x-ray radiation and be visible on a radiographic image.

SUMMARY OF THE INVENTION

In a first aspect of the invention there is provided a medical device made from a material operable to perform a therapeutic function of the device and wherein the material allows three-dimensional visualization of a surrounding tissue when the medical device is inserted into the tissue and viewed under an imaging beam.

It is therefore an object of the invention to provide a medical device that is viewable under certain imaging beams that obviates or mitigates at least one of the above-identified disadvantages of the prior art.

The medical device can be a stent and the surrounding tissue can be a lumen of a blood vessel. The stent can have a coating of a radioopaque material prior to insertion such that the stent that can be viewed during a conventional angiographic x-ray DA/DSA insertion and wherein the coating diminishes after insertion such that the stent can be viewed under CT post insertion. The stent can be coated with at least one of an antibiotic and a chemotherapy drug. The stent can be coated with at least one drug selected from the group consisting of a drug that is therapeutically effective to decrease attachment of platelets to the stent and a drug that is therapeutically effective to decrease restenosis. The drug can be selected from the group consisting of aspirin, plavix or paclitaxel.

In a particular implementation of the first aspect, the device can be selected from the group of devices for the treatment of obstruction due to clot, plaque, atheroma, tumours, and treatments involving intimal hyperplasia and recurrent stenosis.

The material used to manufacture the medical device can be selected from the group consisting of plastic, composite carbon fiber and Inconel, nitinol, stainless steel, or a radio lucent material.

The imaging system can be a substantially real-time CT machine, such as the Toshiba Acquillon.

The medical device can have an image density of less than about 1200 Hounsfield Units. The image density can be less than about 900 Hounsfield Units. The image density can be less than about 700 Hounsfield Units. The image density can be less than about 400 Hounsfield Units.

The medical device can be a microcoil and the surrounding tissue is an aneurysm repaired with the microcoil.

The configuration and structure of the medical device can be chosen to combine with the properties of the chosen material to provide a reduced beam hardened artifact. For example, where the device is a stent and the struts of the stent can be aligned or otherwise configured to reduce the beam hardened artifact.

In another aspect of the invention there is provided an imaging processing unit for a CT machine comprising: [0032] a means for receiving multi-plane images of mammalian tissue; [0033] a database of known medical devices and associated properties of the devices; [0034] a means for determining whether an object detected in the received images matches with a known medical device in the database, the means for determining based on the associated properties; [0035] means for applying a filter to the received images to enhance an image of the tissue that surrounds the implanted medical device based on the known associated properties; and, [0036] means for presenting the image on an output device.

The database of known medical devices can include at least one of a stent and a microcoil. The associated properties in the database can include a Hounsfield unit measurement of the device.

BRIEF DESCRIPTION OF THE DRAWINGS

Embodiments of the invention will now be discussed, by way of example only, with reference to the attached Figures, in which:

FIG. 8 shows a microcoil in accordance with another embodiment of the invention;

FIG. 9 is a partial view of the microcoil of FIG. 8;

DETAILED DESCRIPTION OF THE INVENTION

Figure 1:
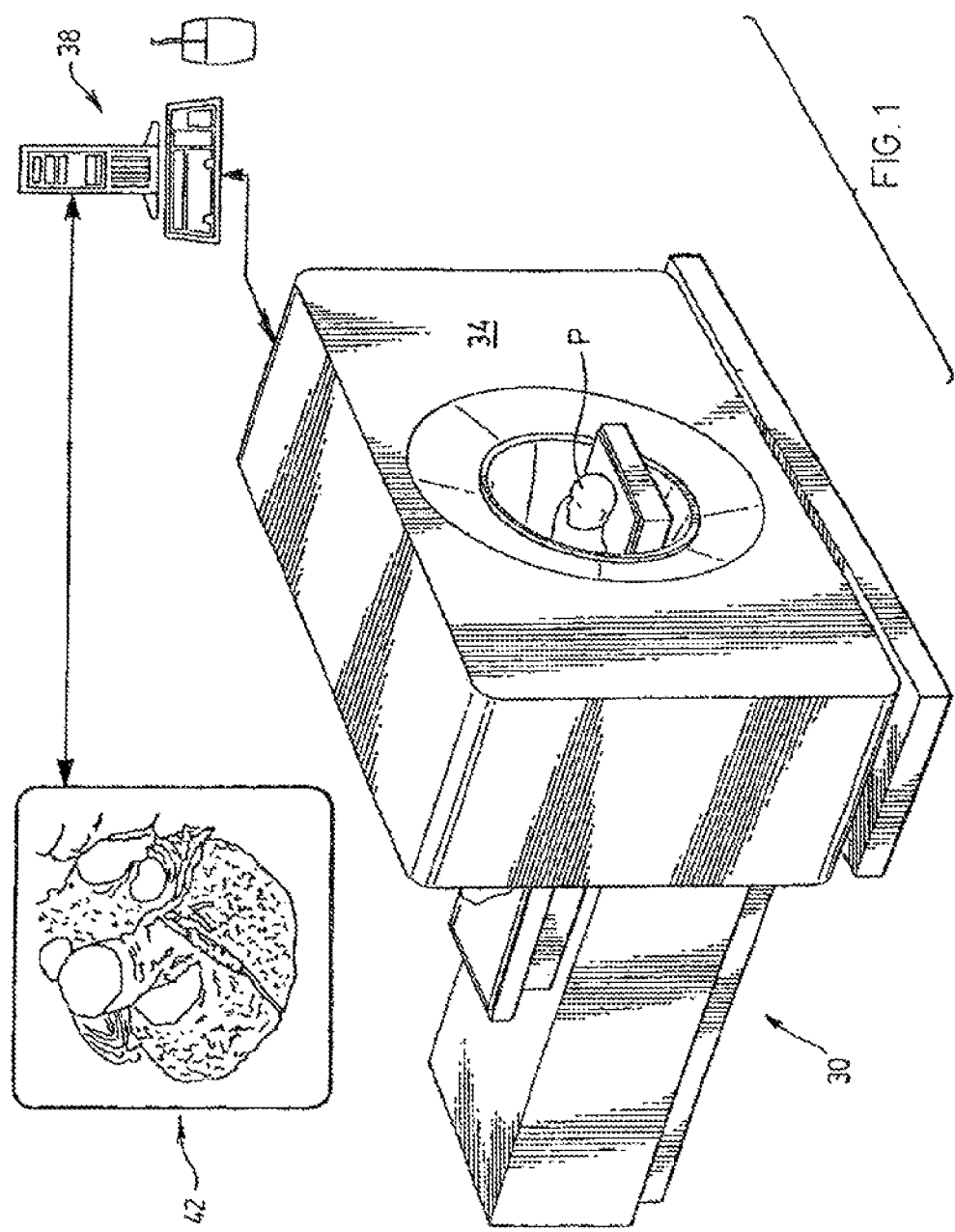
FIG. 1 is a representation of an imaging system.

Referring now to FIG. 1, an imaging system is indicated generally at 30. Imaging system 30 comprises a patient chamber 34, an image processing unit 38 and a display 42. Imaging system 30 can be based on any known or established imaging technology, but in a present embodiment is based on computed tomography (CT) having substantially the same functionality as a machine like the Toshiba Acquillon. Thus, patient chamber 34 is operable to capture images of a patient P in at least three planes, and processing unit 38 is operable to assemble those captured images to present a three-dimensional rendering of a target area within patient P on display 42. Images on display 42 can be navigated and/or viewed using the mouse and keyboard attached to processing unit 38, allowing the user to view a target area within patient P from any number of views. While not shown in FIG. 1, image processing unit 38 can also be attached to other output devices in addition to display 42, such as a printer. Further, image processing unit 38 also typically includes a fixed storage device (such as a hard drive), a removable storage device (such as CD-Rewriter, or a tape drive) and a network interface card or other network interface means for connecting processing unit 38 to a network such as an intranet and/or the internet over which captured images can be delivered.

Figure 2:
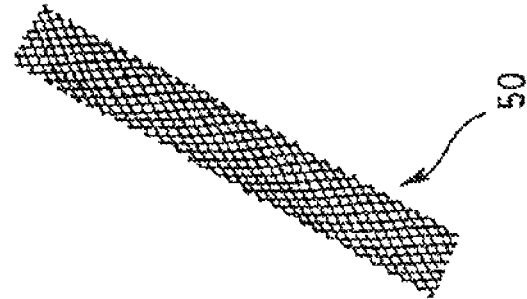
FIG. 2 is a side view of a prior art stent.

Referring now to FIG. 2, a prior art conventional coronary stent is indicated at 50. FIG. 2 shows stent 50 in isolation, however, for purposes of explaining the prior art, it is to be assumed that stent 50 has been implanted in a coronary artery of patent P.

Figure 3:
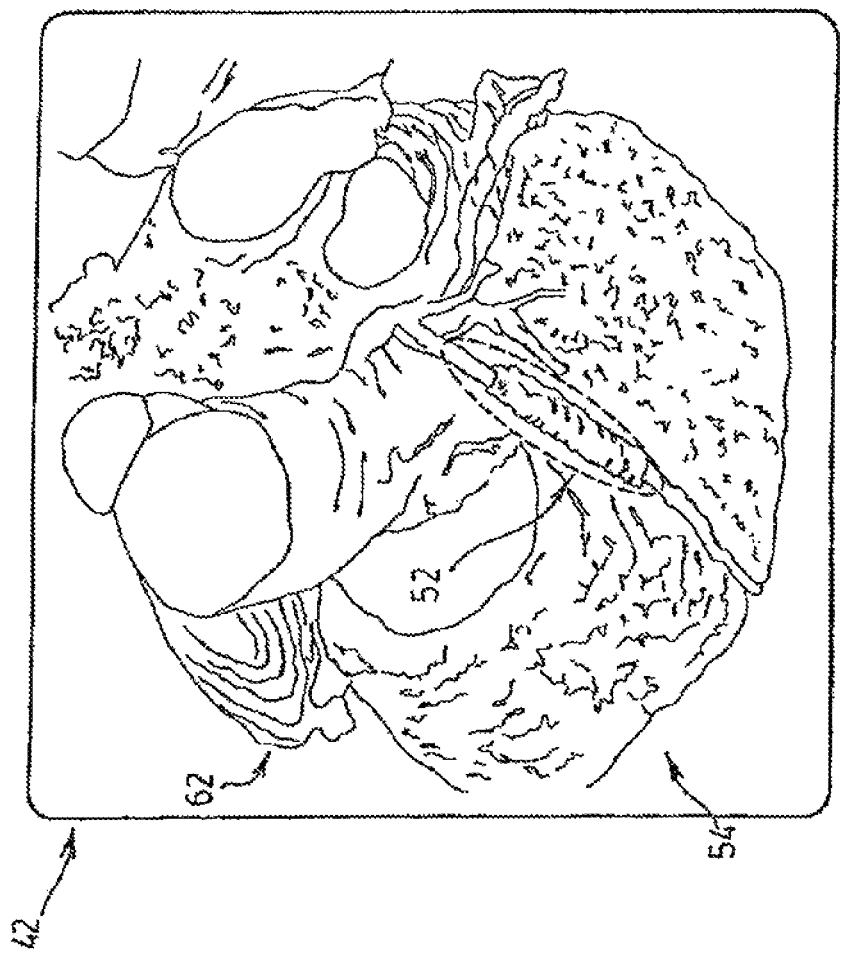
FIG. 3 is a representation of a beam hardened artifact caused by the prior art stent of FIG. 2 when viewed under the imaging system of FIG. 1.

FIG. 3 shows an image 54 rendered on display 42 of system 30 of patient P. Image 54 shows a beam hardened artefact 52 as it is implanted inside a coronary artery 58 inside a heart 62 of patient P. The area identified as beam hardened artefact 52 is an inaccurate reproduction of stent 50 as it is implanted inside artery 58. The beam hardening artefact 52 is created by the material of stent 50. Accordingly, system 30 is of limited value in performing post-operative evaluations of stent 50 and for determining whether any restenosis has occurred of coronary artery 58.

Figure 5:
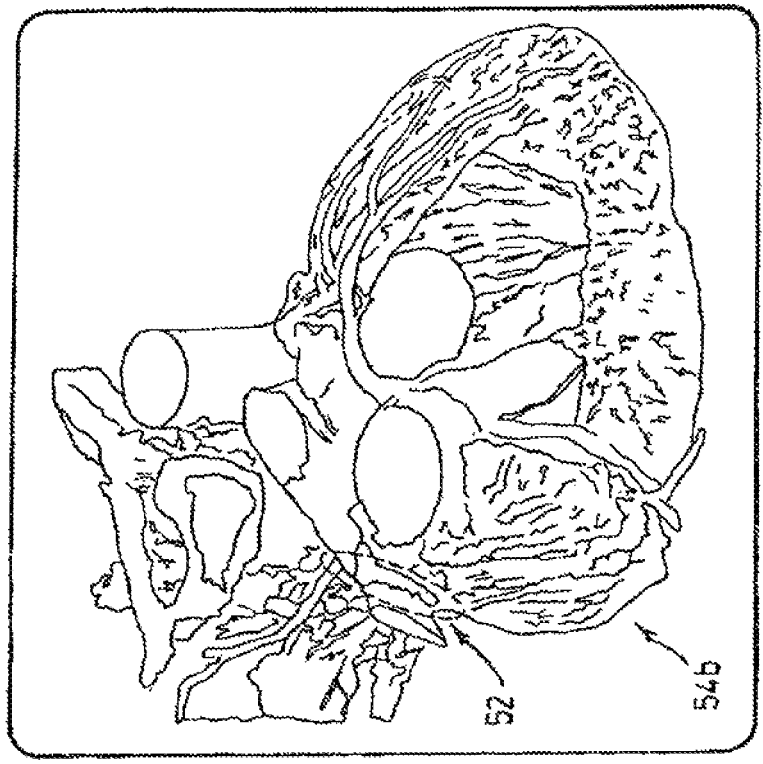
FIG. 5 shows the beam hardened artifact of FIG. 4 at a different angle.
Figure 4:
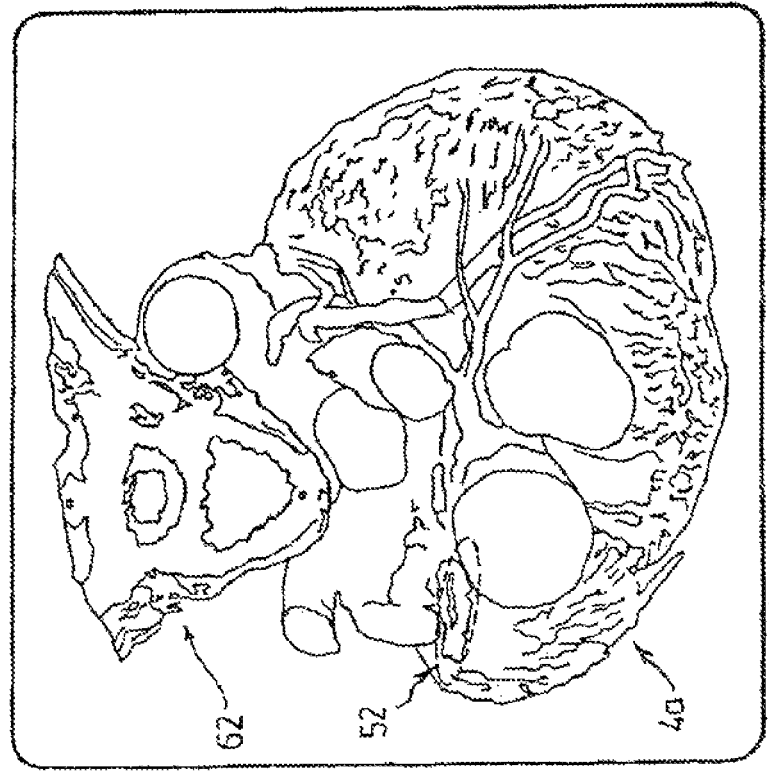
FIG. 4 shows the beam hardened artifact of FIG. 3 at a different angle.

FIGS. 4 and 5 show additional images 54*a* and 54*b*, respectively, of different orientations of heart 62, which are readily produced on display 42 due to the imaging capability of system 30. In each image 54*a* and image 54*b*, stent 50 and the surrounding artery 58 are inaccurately reproduced due to beam hardening artefact 52 of stent 50. Thus, notwithstanding the great flexibility of system 30 in being able to provide a multiplicity of views of heart 62, in its current form stent 50 and system 30 do not provide meaningful images for post-operative evaluation of artery 58 and the progress of any restenosis that may be occurring in the lumen of artery 58 surrounding stent 50.

Figure 7:
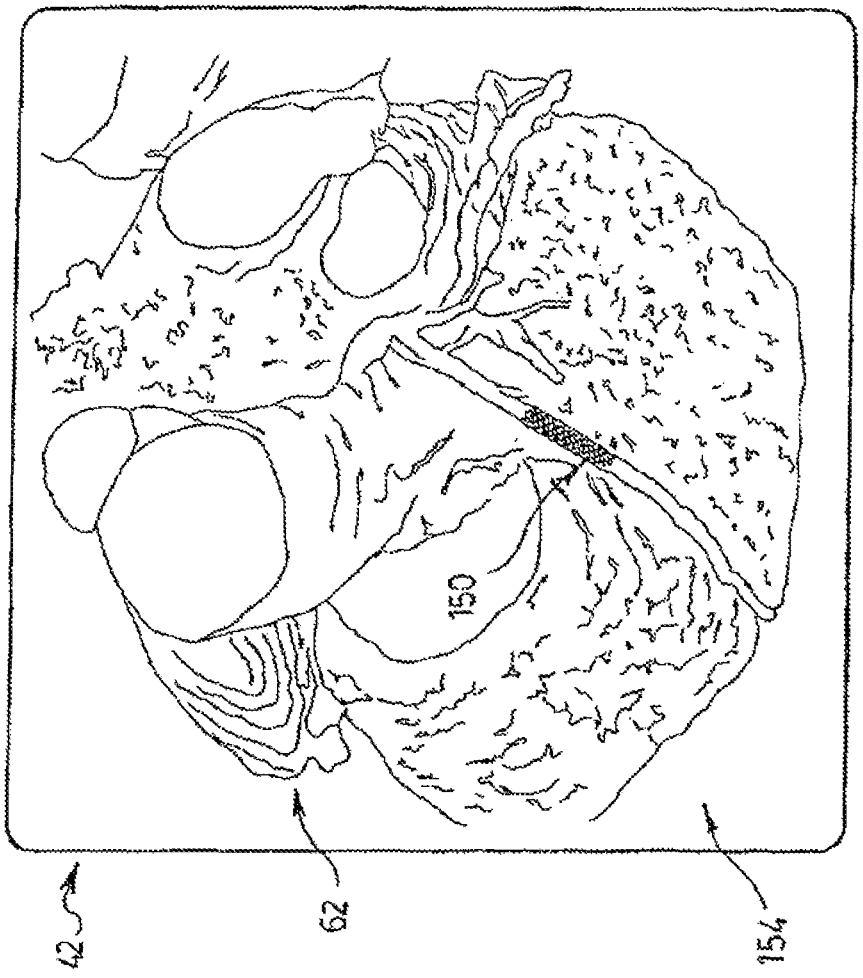
FIG. 7 is a representation of the stent of FIG. 6 when viewed under the imaging system of FIG. 1.
Figure 6:
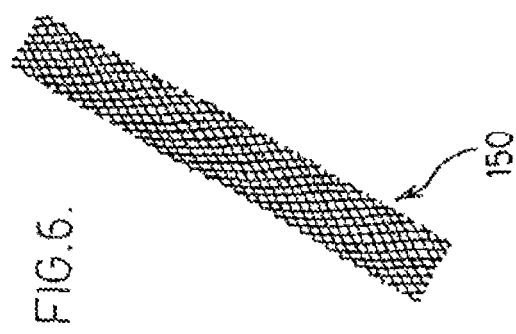
FIG. 6 a side view of a stent in accordance with an embodiment of the invention.

FIG. 6, shows a medical device in accordance with an embodiment of the invention as a stent 150. Stent 150 from outward appearances is substantially the same as prior art stent 50, and indeed, in the present embodiment is designed to provide substantially the same mechanical and therapeutic functionality as prior art stent 50. However, in contrast to prior art stent 50, stent 150 is made from a material that has a selected radiopacity such that the appearance of stent 150 is preserved when stent 150 is exposed to the imaging beam of system 30 and presented on display 42. Thus, when stent 150 is implanted in heart 62, then in an image 154 of heart 62 generated by system 30, the appearance of stent 150 will be maintained when heart 62 and stent 150 are shown in display 42, as shown in FIG. 7. Since image 154 has no beam hardened artefacts, it is now possible to examine the lumen of artery 58 surrounding stent 150, and thereby allow for an examination thereof for restenosis.

As will be appreciated by those of skill in the art, presence or absence of a beam hardening artefact can be measured according to the properties of the imaging system being used and in relation to the Hounsfield units associated with the particular material or tissue being exposed to the imaging beam. A relation between the linear attenuation coefficient (.mu.) and the corresponding Hounsfield unit (H) can be expressed as:

H=.mu.Material–.mu.Water.mu.Water.times.1000
EQU00001##

The value of the Hounsfield unit varies from –1000 (for air) to 1000 (for bone) to 3000, as more particularly shown in Table I.

TABLE-US-00001 TABLE I.sup.1 Tissue Range of Hounsfield units Material Hounsfield Unit Air –1000 Lung –500 to –200 Fat –200 to –50 Water 0 Blood 25 Muscle 25 to 40 Bone 200 to 1000 .sup.1 The foregoing equation and table is found in Principles of Computerized Tomographic Imaging Parallel CT, Fanbeam CT, Helical CT and Multislice CT by Marjolein van der Glas, Aug. 29, 2000, http://www.ph.tn.tudelft.nl/~marlein/pdf/CT.pdf Thus, in certain imaging systems materials with Hounsfield units exceeding about 1000 can be prone to creating beam hardening artefacts. Thus, presently preferred materials from which stent 150 can be manufactured to have reduced beam hardening artefacts include certain plastic, composite carbon fiber and Inconel metals that have similar mechanical properties to prior art stent 50 such that substantially the same therapeutic effect in stent 150 is achieved as was available in prior art stent 50. In any event, the chosen material for stent 150 has a level of Hounsfield density that diminish beam hardening artefacts to substantially preserve the appearance of the device under CT or other corresponding imaging beam.

It is thus presently preferred that stent 150 (or other medical devices according to the present invention) be made from a material or materials to have an overall image density of less than about 1200 Hounsfield Units. Such medical devices can also have an overall image density of less than about 900 Hounsfield Units. Such medical devices can also have an overall image density of less than about 700 Hounsfield Units. Such medical devices can also have an overall image density of less than about 400 Hounsfield Units.

As previously discussed, other medical devices are also within the scope of the present invention. The medical devices within the scope of the invention include devices for the treatment of obstruction due to clot, plaque, atheroma, tumours or the like, and/or treatments involving intimal hyperplasia and recurrent stenosis after stent placement. An appropriate device is delivered into the vascular or bilary system under image guidance. The post placement follow up of the lumen is enabled by the diminished density and beam hardening artefact of the construct and coating of the stent.

A specific example of another medical device within the scope of the invention is shown in FIGS. 8 and 9, which shows a microcoil 250 for treatment of an aneurysm and which is introduced via a guiding cathether 240 and a microcatheter 245. As best seen in FIG. 8, guiding cathether 240 is inserted through an incision 260 near the femoral artery or brachial artery or other suitable location and passed through the venous system of the patient until it reaches a blood vessel 264 proximal to an aneuryism 268 in the patient's head. (Further discussion of this procedure can be found in the Inventor's copending application entitled "Method and Apparatus for Reducing Exposure to an Imaging Beam" and filed in the US Patent Office on Mar. 3, 2003, the contents of which are incorporated herein by reference.)

Figure 10:
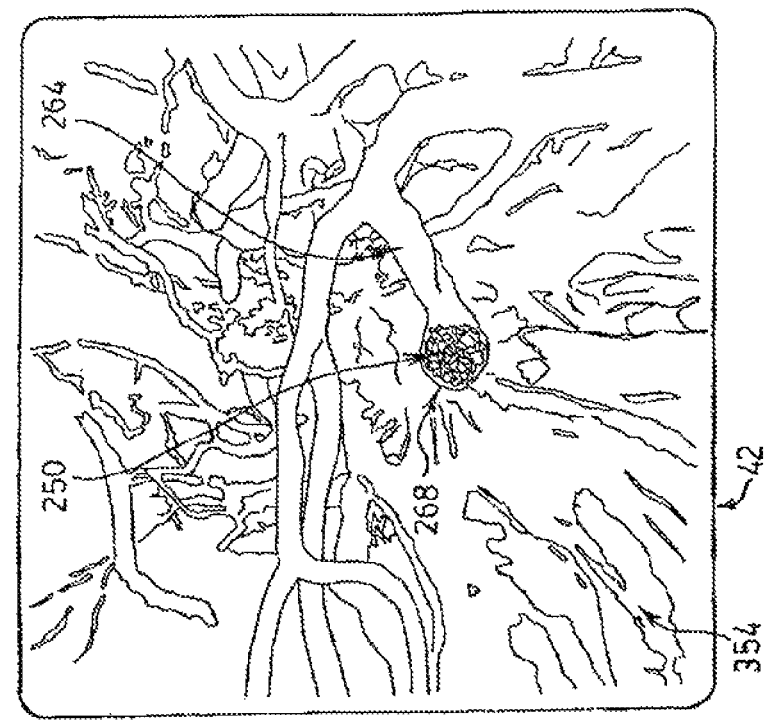
FIG. 10 is a representation of a beam hardened artifact caused by a prior art microcoil when viewed under the imaging system of FIG. 1.

FIG. 10 shows an image 254 of the resulting beam hardened artefact 252 when a prior art microcoil (not shown) is post-operatively examined using imaging system 30 has been previously inserted in the patient according to the method described in reference to FIG. 8. The beam hardened artefact 252 thus renders it difficult, if not impossible, to accurately examine the prior art microcoil using imaging system 30.

Figure 11:
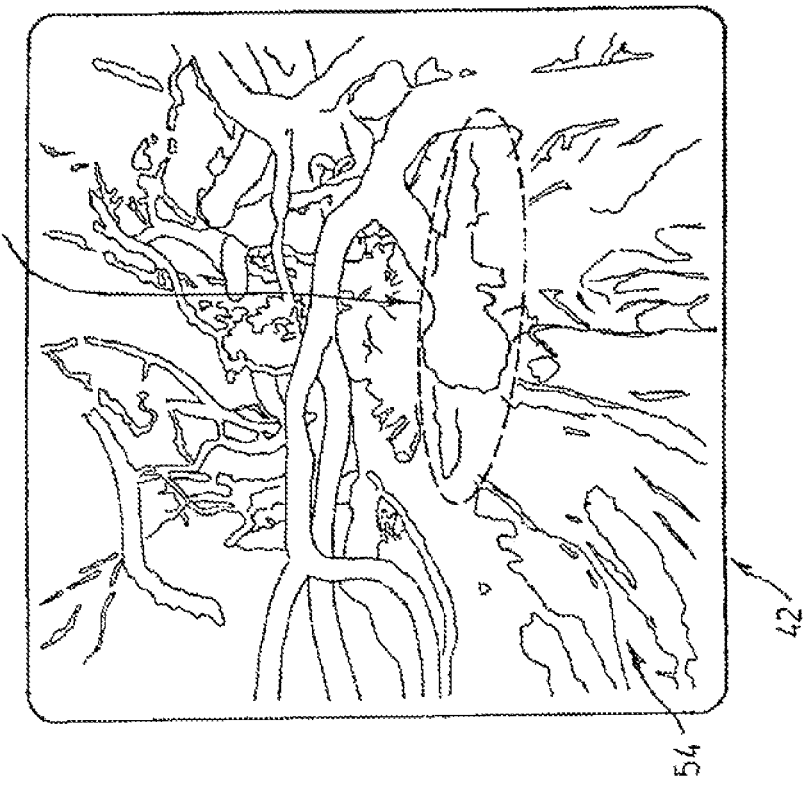
FIG. 11 is a representation of the microcoil of FIG. 9 after insertion into a patient and when viewed under the imaging system of FIG. 1.

However, as seen in image 354 shown in FIG. 11, when microcoil 250 is inserted according to the method described with reference to FIG. 8, then microcoil 250, the now-repaired aneuryism 268 and blood vessel 264 leading thereto are all visible on display 42 and therefore capable of post-operative evaluation.

Figure 12:
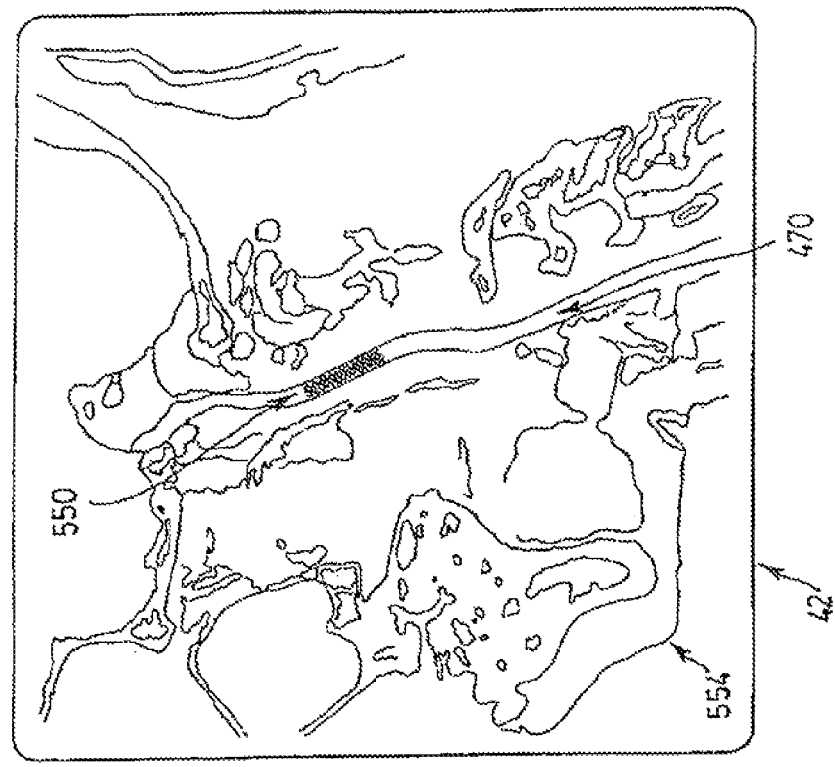
FIG. 12 is a representation of a beam hardened artifact caused by a prior art carotid stent when viewed under the imaging system of FIG. 1; and, FIG. 13 is a representation of a carotid stent in accordance with another embodiment of the invention after the carotid stent has been inserted into a patient and when viewed under the imaging system of FIG. 1.
Figure 13:
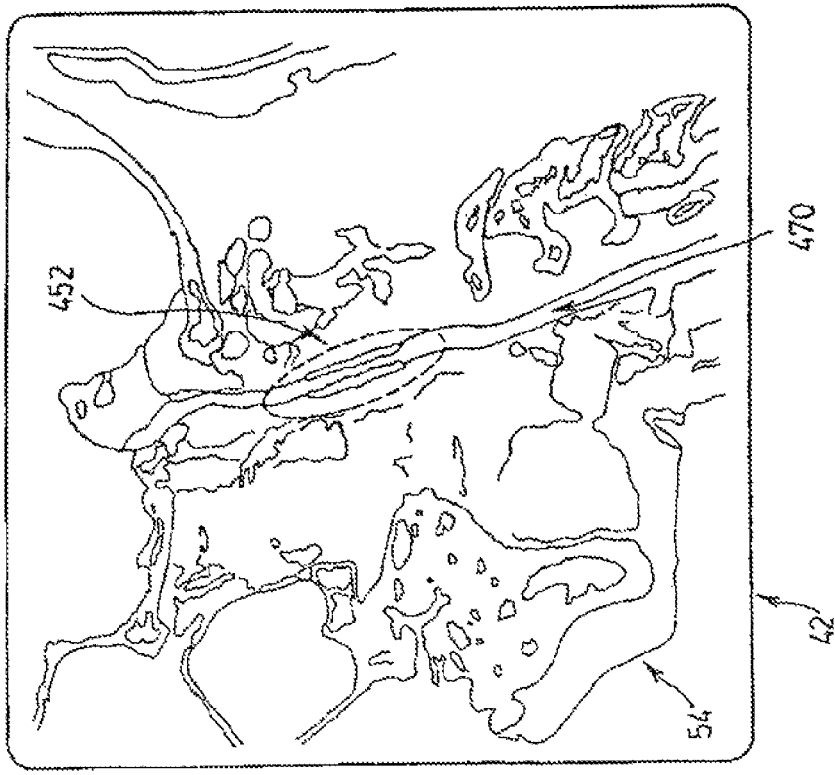

Another medical device within the scope of the invention is a carotid stent, for placement in the carotid artery. FIG. 12 shows an image 454 of a sagittal view of patient along a plane that includes the carotid artery 470 of the patient. Image 454 is characterized by a beam hardened artefact 452 through which the lumen of an implanted prior art stent can be identified, but artefact 452 is severe enough to obscure the lumen of the carotid artery 470, therefore preventing a determination as to whether restenosis is occurring in the lumen of artery 470 surrounding the prior art stent. However, as shown in FIG. 13, when a carotoid stent 550 in accordance with an embodiment of the present invention is used, stent 550 and the lumen of artery 470 surrounding the stent 550 can be viewed and the occurrence of restenonis determined.

In other embodiments of the invention, the specific structure and/or configuration and/or shape of stent 150 (or other medical device) is chosen to further reduce the device's overall radiopacity. For example, the weave of the stent's structure can be chosen to reduce the radiopacity, and therefore the measured level of Hounsfield units associated with the stent. Other aspects of the present invention provide a stent having a reduced number of passages of the stent or devices across the stenosis before dilating and deploying the stent in the stenosis. In certain prior art stents, it is necessary to cross the wire, pre-dilate; and deploy the stent posteriorly. As a further example, a stent in accordance with an embodiment of the present invention can include a self-expanding yet balloon mounted and intelligently be restrained. For example, the stent can be mounted on a balloon that is deployed by inflation of the balloon. Such a stent is self-expanding but is delivered on a balloon. The inflation of the balloon breaks the restraining polymeric bands and results in the self-expansion of the stent once the initial stimulus has been given. This polymeric material is drug-coated and thrombosis resistant. This polymeric material helps restrain plaque and potential embolic material behind the stent. The overall configuration of the stent has reduced beam hardened artifacts post insertion when viewed under CT.

The number of passages of hardware across the stent or devices across the stent is reduced from five (as found in prior art stents) to two (according to an embodiment of the present invention) and thus, restrain against the wall of the vessel deep to the stent the material that would otherwise become potentially an embolic source. This can be helpful in reducing the risks of stroke after carotid stenting and in some circumstances can help reduce the need for distal flow protection devices which themselves have stroke risk.

In another variation of the present invention, shunt 150 is coated (either in its entirety or in particular locations) with an opacifier to temporarily increase the Hounsfield units associated with shunt 150 during its insertion, to allow shunt 150 to be inserted using traditional means. Such a coating would be configured to gradually abate and dissolve into the patient's blood stream, such that the radiopacity and associated Hounsfield units of stent 150 would decrease over time, such that under a post-operative CT evaluation, the Hounsfield units associated with stent 150 are low enough to allow proper visualization of the lumen of artery 58 surrounding stent 150. Suitable materials for coating shunt 150 include gold, iodine, ionic and non ionic iodinated compounds, ethiodol, and lipiodol, barium, tungsten, tantalum, gadolinium. Whatever coating is chosen, the amount and rate of dissolving of the coating is chosen to reduce toxicity experience by the patient during dissolution.

In a presently preferred embodiment, the aforementioned coating is a hydrophilic polymer containing a restenosis inhibiting drug and a density enhancing radiologic material such as lyophilizied iodinated contrast material, which is embedded into the polymer. This coating is then placed over a stent 150 that is made from a suitable material such as a plastic or metal, such as stainless steel, inconel or metal glass (materials already approved by The United States of America Food and Drug Administration), or an optimal arrangement of strands of another metal can be used. The result is that stent 150 is both drug eluting and density eluting (i.e. the level of Hounsfield units associated with the stent decreases over time.)

In another embodiment of the invention, certain post processing software is provided in image processing unit 38 to maximize vascular conspicuity in conjunction with the known Hounsfield units and other imaging properties associated with stent 150 or other medical device in accordance with the present invention. For example, where a level of Hounsfield units associated with stent 150 is known, then upon detection by system 30 of an item within the patient at that particular level of Hounsfield units, then that information can be used to identify the item as stent 150 and then to further enhance the image of the surrounding vascular region based on the known imaging properties (ie. radiopacity, structure, etc.) and using known signal processing an filtering techniques.

While only specific combinations of the various features and components of the present invention have been discussed herein, it will be apparent to those skilled in the art that desired subsets of the disclosed features and components and/or alternative combinations of these features and components can be utilized, as desired. For example, the stents, coils and other medical devices according to the present invention can be coated with a material to decrease the risk of infection and restenosis, using techniques and compounds described in EP0797988A2 and EP1155689A2 to Angiotech Pharmaceuticals Inc. of Canada, and the University of British Columbia.

The present invention also provides certain novel methods for evaluating cervical and intracranial vascular stents using CT, including MDCTA, that is reliable and low cost and then to use these techniques for long term evaluation and outcome analysis of stenting. Sensitivity and specificity can then be determined for MDCTA by comparison to conventional catheter angiogram results. The radiographic density of the stent, coil or other device can be altered to enhance CT, X Ray, Ultrasound and MRI visibility of the lumen. For the purpose of enhanced accuracy of CT diagnostic imaging beam hardening artefacts will be reduced and/or minimized. The devices in the present invention are in contrast to prior art devices that have been developed for conventional fluoroscopy guidance and thus are of a radiodensity or radiopacity that exceeds the needs of CT for clear visualization, this excess density creates unwanted beam hardening artefact.

Furthermore, the present invention allows for a relatively non-invasive means to visualize the lumen of a blood vessel surrounding a previously installed stent (or other site of an implanted medical device). Due to the reduced beam hardening artefacts of the stent, obscuration of the lumen is reduced. This results in the ability to visualize the lumen non-invasively as compared follow-ups conducted by invasive repeat catheter angiography, with its resultant risk of stroke, death and/or injury to an important vessel or to otherwise obscure a critical finding. CTA and CTP are relatively less invasive imaging modalities that have been shown to aid in the diagnosis and treatment of acute ischemic stroke. Both utilize high-speed spiral CT scanning and three-dimensional volumetric reconstruction software to create various types of images following injection of IV contrast solution. CTA can provide three-dimensional vascular delineation similar to other non-invasive techniques as well as visualization of adjacent non-vascular soft-tissue. CTA can also offer rapid volume acquisition, limited reconstruction artifact and scan completion during the period of peak intravascular contrast enhancement. Using CTA, it is often possible to see filling defect in a vessel as a result of contrast displacement by clot or thrombus. The sensitivity for detecting flow abnormality in vessels in the circle of Willis by CTA can be at least 89% when compared to digital subtraction angiography ("DSA"), and CTA does not carry the up to 5% risk of complication, and the up to 0.5% risk of permanent stroke that DSA has been shown to carry.

The above-described embodiments of the invention are intended to be examples of the present invention and alterations and modifications may be effected thereto, by those of skill in the art, without departing from the scope of the invention which is defined solely by the claims appended hereto.

The invention claimed is:

1. A medical device, comprising:
   a component for insertion into a lumen of a blood or lymph vessel, the component having a structure to provide three-dimensional visualization of the lumen when said component is inserted into said lumen and viewed under an imaging beam, said component having:
   (a) a single coating layer including:
     (i) a polymer selected from a group consisting of: a hydrophilic polymer, a hydrophobic polymer, and a fatty acid polymer, and
     (ii) a restenosis inhibiting drug;
   (b) a density enhancing radiologic opacifier embedded into said single coating layer, said single coating layer and said embedded opacifier material together providing a first Hounsfield image density suitable for viewing said component under an imaging beam during insertion of said component into said lumen,
   said density enhancing radiologic opacifier material configured to elute from said single coating layer after insertion into said lumen to provide a second Hounsfield image density lower than said first Hounsfield image density, said second Hounsfield image density being less than about 1200 Hounsfield Units, suitable for viewing a portion said lumen surrounding said component under said imaging beam.

2. The medical device of claim 1, said restenosis inhibiting drug configured to elute at a rate proportional to a rate of elution of said density enhancing radiologic opacifier material, such that residual radiographic density measurements of said component provide a measure of said restenosis inhibiting drug still retained within said polymer.

3. The medical device of claim 1, wherein said density enhancing radiologic opacifier is configured to elute from said component by one of bulk erosion and surface erosion.

4. The medical device of claim 1, wherein said density enhancing radiologic opacifier is a lyophilized iodinated contrast.

5. The medical device of claim 1, wherein said component is constructed of one or more of: stainless steel, carbon fibre, and a plastic.

6. The medical device of claim 1, wherein said component comprises a stent.

7. The medical device of claim 1, wherein said component comprises a microcoil for insertion into an aneurysm in said lumen.

8. The stent of claim 1, wherein said imaging beam comprises CT.

9. The stent of claim 1, wherein said imaging beam comprises MR.

* * * * *

UNITED STATES PATENT AND TRADEMARK OFFICE
CERTIFICATE OF CORRECTION

PATENT NO. : 9,028,543 B2
APPLICATION NO. : 13/919537
DATED : May 12, 2015
INVENTOR(S) : Kieran P. Murphy It is certified that error appears in the above-identified patent and that said Letters Patent is hereby corrected as shown below:

In the specification:

In column 2, line 11: replace "Acquillion" with -- Aquilion --
In column 2, line 21: delete "[0006]"
In column 2, line 26: delete "[0007]"
In column 2, line 29: delete "[0008]"
In column 2, line 33: delete "[0009]"
In column 2, line 38: delete "[0010]"
In column 2, line 43: delete "[0011]"
In column 2, line 47: delete "[0012]"
In column 2, line 42: delete "[0013]"
In column 3, line 20: delete "[0017]"
In column 3, line 23: delete "[0018]"
In column 3, line 24: replace "meointimal" with -- neointimal --
In column 3, line 26: delete "[0019]"
In column 4, line 22: replace "Acquillion" with -- Aquilion --
In column 4, line 38: delete "[0032]"
In column 4, line 39: delete "[0033]"
In column 4, line 40: delete "[0034]"
In column 4, line 44: delete "[0035]"
In column 4, line 47: delete "[0036]"
In column 5, line 30: replace "Acquillion" with -- Aquilion --
In column 6, lines 34-35: replace "H = .mu. Material - .mu. Water .mu. Water .times. 1000 ##EQU00001##" with -- $$H = \frac{\mu Material - \mu Water}{\mu Water} \times 1000$$ --
In column 6, lines 39-46: Replace "TABLE-US-00001 TABLE I.sup.1 Tissue Range of Hounsfield units Material Hounsfield Unit Air -1000 Lung -500 to -200 Fat -200 to -50 Water 0 Blood 25 Muscle 25 to 40 Bone 200 to 1000 .sup.1 The foregoing equation and table is found in Principles of Computerized Tomographic Imaging Parallel CT, Fanbeam CT, Helical CT and Multislice CT by Signed and Sealed this
Twenty-third Day of February, 2016

Michelle K. Lee
*Director of the United States Patent and Trademark Office*

Marjolein van der Gias, Aug. 29, 2000, http://www.ph.tn.tudelft.nl/~ marlein/pdf/CT.pdf" with

TABLE I[1]

| Tissue Range of Hounsfield units | |
|---|---|
| Material | Hounsfield Unit |
| Air | −1000 |
| Lung | −500 to −200 |
| Fat | −200 to −50 |
| Water | 0 |
| Blood | 25 |
| Muscle | 25 to 40 |
| Bone | 200 to 1000 |

[1]The foregoing equation and table is found in *Principles of Computerized Tomographic Imaging Parallel CT, Fanbeam CT, Helical CT and Multislice CT* by Marjolein van der Glas, Aug. 29, 2000, http://www.ph.tn.tudelft.nl/~marlein/pdf/CT.pdf In the claims:

In Column 10, line 48: Replace "stent" with -- medical device --
In Column 10, line 50: Replace "stent" with -- medical device --